US008473035B2

(12) United States Patent
Frangioni

(10) Patent No.: US 8,473,035 B2
(45) Date of Patent: Jun. 25, 2013

(54) MEDICAL IMAGING SYSTEMS

(75) Inventor: John V. Frangioni, Wayland, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1206 days.

(21) Appl. No.: 10/572,169

(22) PCT Filed: Sep. 15, 2003

(86) PCT No.: PCT/US03/29368
§ 371 (c)(1),
(2), (4) Date: Dec. 22, 2006

(87) PCT Pub. No.: WO2005/034747
PCT Pub. Date: Apr. 21, 2005

(65) Prior Publication Data
US 2007/0203413 A1 Aug. 30, 2007

(51) Int. Cl.
*A61B 6/00* (2006.01)
(52) U.S. Cl.
USPC .......................................................... 600/476
(58) Field of Classification Search
USPC .......................................................... 600/476
See application file for complete search history.

(56) References Cited

U.S. PATENT DOCUMENTS

| 4,807,026 | A | | 2/1989 | Nishioka et al. | |
|---|---|---|---|---|---|
| 4,821,117 | A | | 4/1989 | Sekiguchi | |
| 5,120,953 | A | | 6/1992 | Harris | |
| 5,323,009 | A | | 6/1994 | Harris | |
| 5,526,814 | A | * | 6/1996 | Cline et al. | 600/411 |
| 5,582,576 | A | | 12/1996 | Hori et al. | |
| 5,827,190 | A | | 10/1998 | Palcic et al. | |
| 5,954,650 | A | * | 9/1999 | Saito et al. | 600/425 |
| 6,018,565 | A | * | 1/2000 | Ergun et al. | 378/95 |
| 6,061,591 | A | | 5/2000 | Freitag et al. | |
| 6,099,466 | A | | 8/2000 | Sano et al. | |
| 6,167,297 | A | | 12/2000 | Benaron | |
| 6,192,269 | B1 | | 2/2001 | Okumura et al. | |
| 6,212,425 | B1 | | 4/2001 | Irion et al. | |
| 6,284,223 | B1 | | 9/2001 | Luiken | |
| 6,289,236 | B1 | | 9/2001 | Koenig et al. | |
| 6,293,911 | B1 | * | 9/2001 | Imaizumi et al. | 600/160 |
| 6,334,847 | B1 | * | 1/2002 | Fenster et al. | 600/443 |
| 6,671,540 | B1 | | 12/2003 | Hochman | |
| 6,775,565 | B1 | | 8/2004 | Wieringa | |

(Continued)

FOREIGN PATENT DOCUMENTS

| WO | WO-2005/079662 A1 | 9/2005 |
|---|---|---|
| WO | WO-2008042486 A2 | 4/2008 |

OTHER PUBLICATIONS

Paint Shop Pro 7, Copyright 2000, COREL/JASC, Version 7.*

(Continued)

*Primary Examiner* — Tse Chen
*Assistant Examiner* — Hien Nguyen
(74) *Attorney, Agent, or Firm* — Edwards Wildman Palmer LLP; Peter F. Corless; Stephen D. LeBarron

(57) ABSTRACT

A medical imaging system provides simultaneous rendering of visible light and diagnostic or functional images. The system may be portable, and may include adapters for connecting various light sources and cameras in open surgical environments or laparascopic or endoscopic environments. A user interface provides control over the functionality of the integrated imaging system. In one embodiment, the system provides a tool for surgical pathology.

19 Claims, 8 Drawing Sheets

Fig. 7

U.S. PATENT DOCUMENTS

| | | |
|---|---|---|
| 6,804,549 B2 | 10/2004 | Hayashi |
| 6,898,458 B2 | 5/2005 | Zeng et al. |
| 6,915,154 B1 | 7/2005 | Docherty et al. |
| 7,014,994 B1 * | 3/2006 | Barany et al. ............ 435/6.12 |
| 2001/0007920 A1 | 7/2001 | Hayashi |
| 2002/0090119 A1 | 7/2002 | Saito et al. |
| 2003/0078477 A1 | 4/2003 | Kang et al. |
| 2002/0900119 | 7/2003 | Saito et al. |
| 2003/0187319 A1 | 10/2003 | Kaneko et al. |
| 2004/0022447 A1 * | 2/2004 | Mukhopadhyay et al. ... 382/243 |
| 2004/0245350 A1 | 12/2004 | Zeng |
| 2005/0065430 A1 | 3/2005 | Wiethoff et al. |
| 2005/0182321 A1 | 8/2005 | Frangioni |

OTHER PUBLICATIONS

"U.S. Appl. No. 10/507,253, Non-Final Office Action mailed Oct. 2, 2008.", OARN, 18 pgs.

"Application Serial No. PCT/US03/29368", PCT Search Report mailed Oct. 23, 2003, all.

"U.S. Appl. No. 10/507,253 Final Office Action mailed Apr. 14, 2009", 11 pgs.

"U.S. Appl. No. 10/507,253, Non Final Office Action mailed Oct. 23, 2009", 12.

* cited by examiner

US 8,473,035 B2

MEDICAL IMAGING SYSTEMS

GOVERNMENT INTERESTS

The United States Government may have certain rights in this invention pursuant to National Institute of Health Grant # R21CA88245 and Department of Energy Grant # DE-FG02-01ER63188.

CROSS-REFERENCE TO RELATED APPLICATIONS

This application is a national stage filing under 35 U.S.C. 371 of International Application PCT/US03/029368 filed Sep. 15, 2003, the specification of which is hereby incorporated by reference in its entirety. International Application PCT/US03/029368 was published under PCT Article 21(2) in English.

BACKGROUND OF THE INVENTION

Absorption and fluorescent dyes, such as indocyanine green, have proven useful for medical imaging applications. Some of the more commonly used dyes share a number of useful characteristics. First, the dyes are suitable for labeling antibodies or low-molecular-weight ligands of diagnostic significance, or otherwise adapted for sequestration or preferential uptake at a site of interest such as a lesion. The dyes are safe for injection or other introduction into a live subject. And finally, the dyes emit light at a specific wavelength when excited, so that their location and concentration may be tracked.

A number of imaging systems have been devised to detect and display these dyes within living tissue. For example, dyes such as indocyanine green have been used to visualize blood flow in eyes. In some cases, such as U.S. Pat. No. 6,293,911 to Imaizumi et al., a dye imaging device has been combined with a visible light imaging system. Imaizumi describes endoscopic tools that generate images of dye-labeled antibodies superimposed over visible light images captured from within the body. As a disadvantage, the Imaizumi patent discloses a system with complex optics and hardware, and does not teach how the system might be adapted for use in open surgical applications such as surgical pathology.

There remains a need for improved surgical and diagnostic imaging tools capable of generating functional images concurrent with visible light images of a subject.

SUMMARY OF THE INVENTION

A medical imaging system provides simultaneous rendering of visible light and diagnostic, or functional, images. The system may be portable, and may include adapters for connecting various light sources and cameras in open surgical environments or laparascopic or endoscopic environments. A user interface provides control over the functionality of the integrated imaging system. In one embodiment, the system provides a tool for surgical pathology.

BRIEF DESCRIPTION OF DRAWINGS

The invention will be appreciated more fully from the following further description thereof, with reference to the accompanying drawings, wherein.

DETAILED DESCRIPTION OF CERTAIN EMBODIMENTS OF THE INVENTION

To provide an overall understanding of the invention, certain illustrative embodiments will now be described, including a system for generating superimposed circulatory and tissue images in video format. However, it will be understood that the methods and systems described herein can be suitably adapted to other medical imaging applications where visible light tissue images may be usefully displayed with diagnostic image information obtained from outside the visible light range and superimposed onto the visible light image. More generally, the methods and systems described herein may be adapted to any imaging application where a visible light image may be usefully displayed with a superimposed image captured from areas within the visible light image that are functionally marked to emit photons outside the visible light range (or in certain circumstances, within a specific band of visible light wavelengths) by a dye or other material. For example, the systems and methods are applicable to a wide range of diagnostic or surgical applications where a target pathology, tissue type, or cell may be labeled with a fluorescent dye or other fluorescent substance. These and other applications of the systems described herein are intended to fall within the scope of the invention.

Terms such as "functional image," "diagnostic image," and "emission wavelength image" are intended to refer to the image captured from photons emitted by the markers (e.g., dyes or other substances) described herein. Unless otherwise specified, these terms are used interchangeable. Terms such as "combined image," "superimposed image", and "merged image" are intended to refer to an image combining the visible light image and the functional image into a single image that may be displayed to a user. Unless otherwise specified, these terms are used interchangeably.

Figure 1:
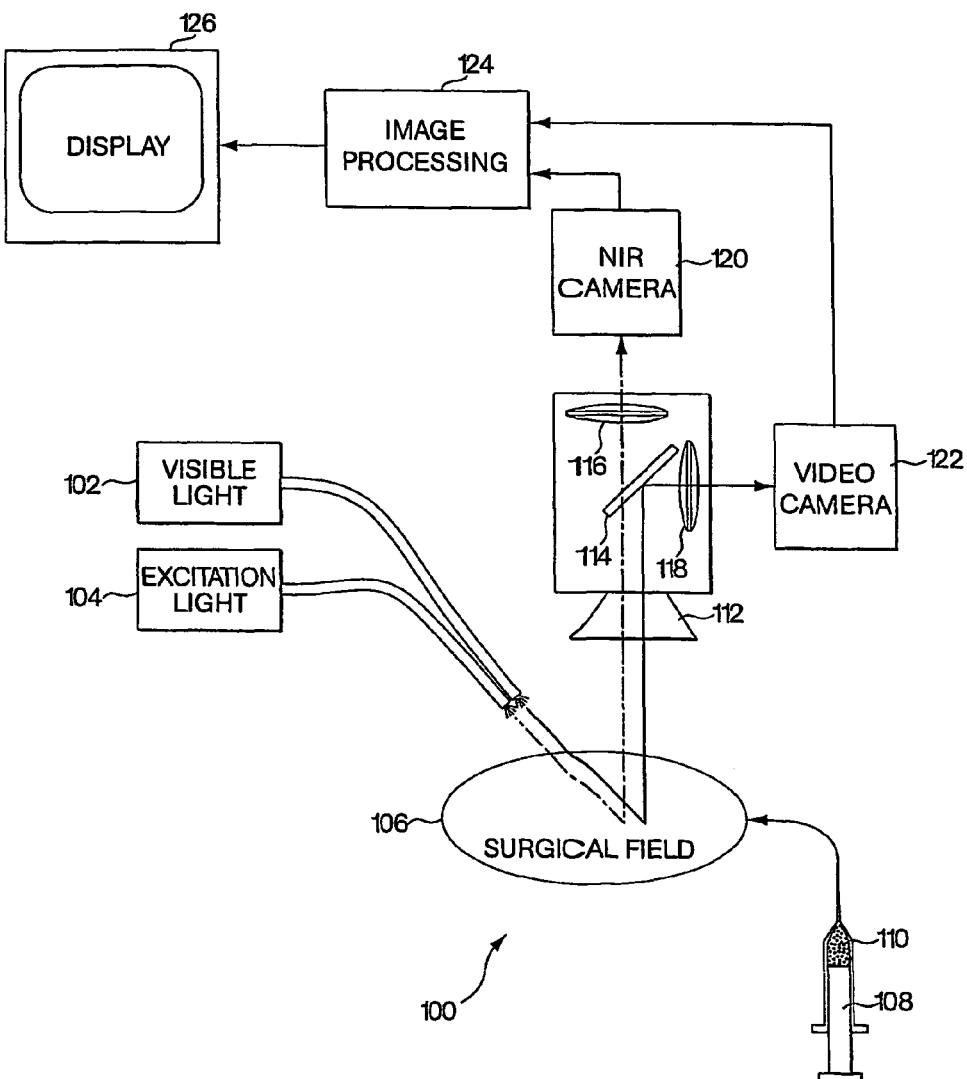
FIG. 1 shows an embodiment of an imaging system for use during open surgery.

FIG. 1 shows an embodiment of an imaging system for use during open surgery. The imaging system 100 may include a visible light source 102, and excitation light source 104, a surgical field 106, a dye source 108 containing a dye 110, a lens 112, a first filter 114, a second filter 116, a third filter 118, a near-infrared camera 120, a video camera 122, an image processing unit 124, and a display 126. In general, the visible light source 102 and the excitation light source 104 illuminate the surgical field 106. The dye 110 may be introduced from the dye source 108, such as through injection into the bloodstream of a subject. An image from the surgical field 106 is then captured by two cameras, the video camera 122 capturing a conventional, visible light image of the surgical field 106 and the near-infrared camera 120 capturing a diagnostic image based upon the distribution of the dye 110 in the surgical field 106. These images may be combined by the image processing unit 124 and presented on a display 126 where they may be used, for example, by a surgeon conducting a surgical procedure. Each aspect of the system 100 is now described in more detail.

The imaging system 100 may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose the surgical field 106, light sources 102, 104, and cameras 120, 122 in an area that is not exposed to broadband light sources. This may be achieved by using an operating room closed to external light sources, or by using a hood or other enclosure or covering for the surgical field 106 that prevents invasion by unwanted spectrum. The visible light source 102 may then serve as a light source for the visible light camera 122, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a closed body cavity, and do not include an operating area as that term is intended herein.

The visible light source 102 may be, for example, a near-infrared depleted white light source. This may be a one-hundred fifty Watt halogen lamp with one or more filters to deplete wavelengths greater than 700 nanometers ("nm"). Generally, any light source constrained to wavelengths between 400 nm and 700 nm may operate as the visible light source 102. In certain applications, the excitation light source 104 and resulting emission from the dye 110 may have wavelengths near or below 700 nm, as with Cy5 dye, which emits light when excited at 650 nm. These near-red dyes may be used with the present system, however, this requires a visible light source 102 that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source should be depleted at the wavelength(s) of interest. As such, the visible light source 102 should more generally be understood to be a source of light that includes some, but not necessarily all, of the wavelengths of visible light.

It should also be understood that, in a far-red imaging system or infrared imaging system such as those noted above, the near-infrared camera 120 described in the example embodiment will instead be a camera sensitive to the emission wavelength of the dye 110 or other fluorescent substance, and that other modifications to light sources, filters and other optics will be appropriate. Similar modifications may be made to isolate a band of wavelengths for dye excitation and emission anywhere within or outside the visible light range, provided that suitable optics, cameras, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source 104 and the emission camera, the near-infrared camera 120 in the example embodiment, for such applications. Cameras sensitive to far-red, near-infrared, and infrared wavelengths are commercially available.

The excitation light source 104 provides light at a wavelength that excites the dye 110. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by the video camera 122 or the emission wavelength of the dye 110. The near-infrared band is generally understood to include wavelengths between 700 nm and 1000 nm, and is a useful wavelength range for a number of readily available excitation light sources 104 and dyes 110 that may be used with the systems described herein. Suitable optical coupling and lenses may be provided to direct each of the visible light source 102 and the excitation light source 104 at an area of interest within the surgical field 106.

The surgical field 106 may be any area of a subject or patient that is open for a surgical procedure. This may be, for example, an open chest during a procedure such as a revascularization or cardiac gene therapy, where visualization of the circulatory system may improve identification of areas at risk for myocardial infarction. Blood flow visualization may permit an assessment of coronary arteries during a coronary artery bypass graft, or an assessment of blood flow and viability during introduction of genes for endothelial growth factor or fibroblast growth factor to induce neovascularization within ischemic regions of the heart. More generally, the surgical field 106 may include any areas of a patient's body, such as a region of the body that includes a tumor that is to be surgically removed, and that is amenable to visualization with fluorescent dyes, such as through the use of labeled antibodies.

The dye source 108 may be any instrument used for injection or other introduction of the dye 110 into a subject, such as a hypodermic needle or angiocath. Where, for example, the dye 110 is highly soluble in blood, the dye source 108 may be administered anywhere on the subject, and need not be near the surgical field 106. For example, it has been found that IRDye78-CA (the carboxylic acid form of IRDye78), when injected intravenously into a live laboratory rat, produced peak vasculature image strength of an open heart approximately 5-10 seconds after injection, and remained adequate for visualization for over one minute. In certain embodiments, the dye source 108 may not use injection. For example, the dye source 108 may spray or otherwise apply the dye 110 to an area of interest. Depending upon the type of dye and the imaging technique, the dye 110 may be delivered in a discrete dose, or may be continuously or intermittently applied and re-applied by the dye source 108.

The dye 110 may be any dye suitable for use in vivo and having excitation and emission wavelengths suitable for other components of the system 100. Typically, the dye 110 will be diluted to 25-50 µM for intravenous injection, such as with phosphate buffered saline, which may be supplemented with Cremophor EL (Sigma) and/or absolute ethanol. A number of suitable near-infrared dyes are described below.

'Acyl' refers to a group suitable for acylating a nitrogen atom to form an amide or carbamate, a carbon atom to form a ketone, a sulfur atom to form a thioester, or an oxygen atom to form an ester group, e.g., a hydrocarbon attached to a —C(=O)-moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The terms 'amine' and 'amino' are art-recognized and refer to both unsubstituted and substituted amines as well as ammonium salts, e.g., as can be represented by the general formula:

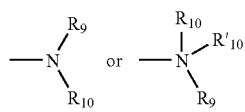

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, e.g., $R_9$, $R_{10}$, and $R'_{10}$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R'_{10}$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

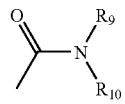

wherein $R_9$ and $R_{10}$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substitutents. Preferred alkyls are unsubstituted. Preferred substituted alkyls are mono-, di-, or trisubstituted. Preferred alkyl substitutents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group. Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocyclic aliphatic, or —O-heterocyclic aliphatic.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substitutents on the ring. Preferred aromatic ring substitutents include: halo, cyano, lower alkyl, heteroalkyl, haloalkyl, phenyl, phenoxy, or any combination thereof. More preferred substitutents include lower alkyl, cyano, halo, and haloalkyl.

'Cycloalkyl ring' refers to a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 4 to about 10 carbon atoms, preferably from 4 to 7 carbon atoms, and most preferably from 5 to 6 carbon atoms in the ring. Bicyclic cycloalkyl rings contain from 8 to 12 carbon atoms, preferably from 9 to 10 carbon atoms in the ring. Cycloalkyl rings may be unsubstituted or substituted with from 1 to 4 substitutents on the ring. Preferred cycloalkyl ring substitutents include halo, cyano, alkyl, heteroalkyl, haloalkyl, phenyl, phenoxy or any combination thereof. More preferred substitutents include halo and haloalkyl. Preferred cycloalkyl rings include cyclopentyl, cyclohexyl, cyclohexenyl, cycloheptyl, and cyclooctyl. More preferred cycloalkyl rings include cyclohexyl, cycloheptyl, and cyclooctyl.

The term 'carbonyl' is art-recognized and includes such moieties as can be represented by the general formula:

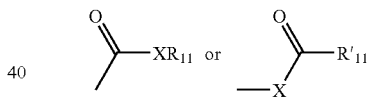

wherein X is a bond or represents an oxygen or a sulfur, and $R_{11}$ represents a hydrogen, hydrocarbon substituent, or a pharmaceutically acceptable salt, $R_{11'}$ represents a hydrogen or hydrocarbon substituent. Where X is an oxygen and $R_{11}$ or $R_{11'}$ is not hydrogen, the formula represents an 'ester'. Where X is an oxygen, and $R_{11}$ is as defined above, the moiety is referred to herein as a carboxyl group, and particularly when $R_{11'}$ is a hydrogen, the formula represents a 'carboxylic acid'. Where X is an oxygen, and $R_{11'}$ is hydrogen, the formula represents a 'formate'. In general, where the oxygen atom of the above formula is replaced by sulfur, the formula represents a 'thiocarbonyl' group. Where X is a sulfur and $R_{11}$ or $R_{11'}$ is not hydrogen, the formula represents a 'thioester.' Where X is a sulfur and $R_{11}$ is hydrogen, the formula represents a 'thiocarboxylic acid.' Where X is a sulfur and $R_{11'}$ is hydrogen, the formula represents a 'thioformate.' On the other hand, where X is a bond, $R_{11}$ is not hydrogen, and the carbonyl is bound to a hydrocarbon, the above formula represents a 'ketone' group. Where X is a bond, $R_{11}$ is hydrogen, and the carbonyl is bound to a hydrocarbon, the above formula represents an 'aldehyde' or 'formyl' group.

'Ci alkyl' is an alkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substitutents. Preferred halo are fluoro, chloro and bromo; more preferred are chloro and fluoro.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di- C1-C3 alkylamino, methylphenylamino, methylbenzylamino, C1-C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substitutents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substitutents. Preferred substituents include lower alkyl, lower heteroalkyl, cyano, halo, and haloalkyl.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term 'nitro' means —NO$_2$.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

The term 'sulfate' is art-recognized and includes a moiety that can be represented by the general formula:

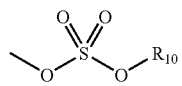

in which $R_{10}$ is as defined above.

A 'substitution' or 'substituent' on a small organic molecule generally refers to a position on a multivalent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and nonaromatic organic compounds which can be substituted or unsubstituted.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

In certain embodiments, the subject method employs a fluorescent dye having a structure of the formula:

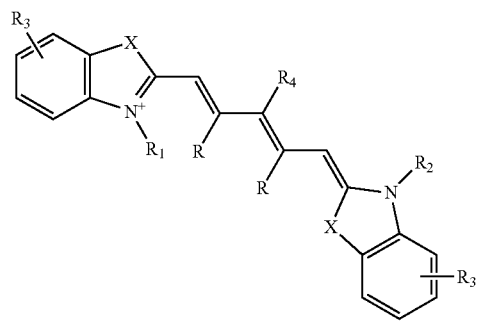

wherein, as valence and stability permit,

X represents $C(R)_2$, S, Se, O, or $NR_5$;

R represents H or lower alkyl, or two occurrences of R, taken together, form a ring together with the carbon atoms through which they are connected;

R₁ and R₂ represent, independently, substituted or unsubstituted lower alkyl, lower alkenyl, cycloalkyl, cycloalkylalkyl, aryl, or aralkyl, e.g., optionally substituted by sulfate, phosphate, sulfonate, phosphonate, halogen, hydroxyl, amino, cyano, nitro, carboxylic acid, amide, etc., or a pharmaceutically acceptable salt thereof;

R₃ represents, independently for each occurrence, one or more substitutents to the ring to which it is attached, such as a fused ring (e.g., a benzo ring), sulfate, phosphate, sulfonate, phosphonate, halogen, lower alkyl, hydroxyl, amino, cyano, nitro, carboxylic acid, amide, etc., or a pharmaceutically acceptable salt thereof;

R₄ represents H, halogen, or a substituted or unsubstituted ether or thioether of phenol or thiophenol; and R₅ represents, independently for each occurrence, substituted or unsubstituted lower alkyl, cycloalkyl, cycloalkylalkyl, aryl, or aralkyl, e.g., optionally substituted by sulfate, phosphate, sulfonate, phosphonate, halogen, hydroxyl, amino, cyano, nitro, carboxylic acid, amide, etc., or a pharmaceutically acceptable salt thereof.

Dyes representative of this formula include indocyanine green, as well as:

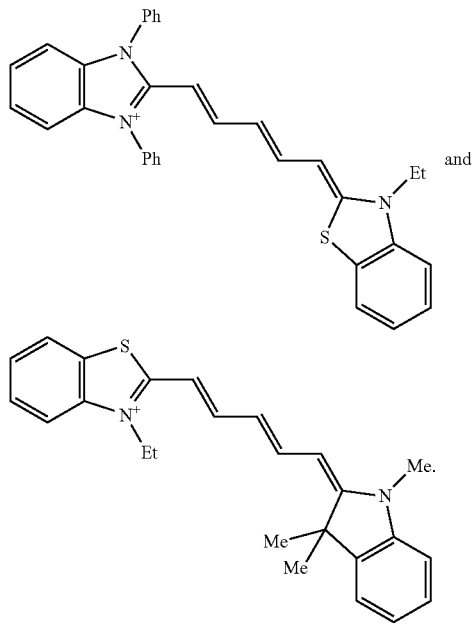

In certain embodiments wherein two occurrences of R taken together form a ring, the ring is six-membered, e.g., the fluorescent dye has a structure of formula:

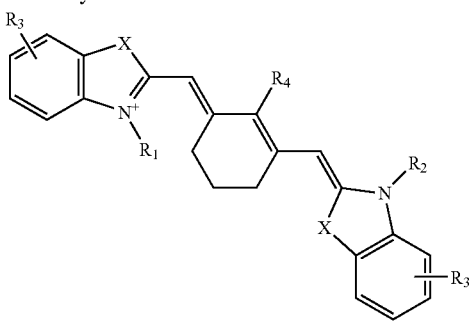

wherein X, R₁, R₂, R₃, R₄, and R₅ represent substituents as described above.

Dyes representative of this formula include IRDye78, IRDye80, IRDye38, IRDye40, IRDye41, IRDye700, IRDye800, Cy7 (AP Biotech), and compounds formed by conjugating a second molecule to any such dye, e.g., a protein or nucleic acid conjugated to IRDye800, IRDye40, or Cy7, etc. The IRDyes are commercially available from Li-Cor Biosciences of Lincoln, Nebr., and each dye has a specified peak absorption wavelength (also referred to herein as the excitation wavelength) and peak emission wavelength that may be used to select suitable optical hardware for use therewith. It will be appreciated that other dyes may also be used, including the far-red dyes noted above, provided suitable adjustments are made to the visible light imaging components of the system 100, and other near-infrared dyes or infrared substances such as the previously mentioned quantum dots. Several specific dyes suited for specific imaging techniques are now described.

IRDye78-CA is useful for imaging the vasculature of the tissues and organs. The dye in its small molecule form is soluble in blood, and has an in vivo early half-life of several minutes. This permits multiple injections during a single procedure. Indocyanine green has similar characteristics, but is somewhat less soluble in blood and has a shorter half-life. IRDye78 may also be used in other imaging applications, since it can be conjugated to tumor-specific ligands for tumor visualization. More generally, IRDye78 may be linked to an antibody, antibody fragment, or ligand associated with a tumor. Presence of the tumor or lesion may then be visualized using the techniques described above.

As another example, IR-786 partitions efficiently into mitochondria and/or endoplasmic reticulum in a concentration-dependent manner, thus permitting blood flow and ischemia visualization in a living heart. The dye has been successfully applied, for example, to image blood flow in the heart of a living laboratory rat after a thoracotomy. More generally, IR-786 may be used for non-radioactive imaging of areas of ischemia in the living heart, or other visualization of the viability of other tissues.

While a number of suitable dyes have been described, it should be appreciated that such fluorescent dyes are examples only, and that more generally, any fluorescent substance may be used with the imaging systems described herein, provided the substance has an emission wavelength that does not interfere with visible light imaging. This includes the fluorescent dyes described above, as well as substances such as quantum dots which may have emission wavelengths above 1000 nm, and may be associated with an antibody, antibody fragment, or ligand and imaged in vivo. All such substances are referred to herein as fluorescent substances, and it will be understood that suitable modifications may be made to components of the imaging system for use with any such fluorescent substance.

The lens 112 may be any lens suitable for receiving light from the surgical field 106 and focusing the light for image capture by the near-infrared camera 120 and the video camera 122. The lens 112 may include one or more optical coatings suitable for the wavelengths to be imaged, and may provide for manual, electronically-assisted manual, or automatic control of zoom and focus.

The first filter 114 may be positioned in the image path from the lens 112 such that a visible light image having one or more visible light wavelengths is directed toward the video camera 122, either by reflection or transmittance. An emission image from the excited dye 110 passes through the lens 112 and is directed toward the near infrared camera 120, again either through reflection or transmittance. A number of arrangements of the cameras 120, 122 and the first filter 114 are possible, and may involving reflecting or transmitting either the visible light image or the emission wavelength image (also referred to herein as the diagnostic image).

In one embodiment, IRDye78-CA (carboxylic acid) having a peak absorption near 771 nm and a peak emission near 806 nm, is used with the system 100. In this embodiment, the first filter 114 may be a 785 nm dichroic mirror that transmits near-infrared light and reflects visible light. The first filter 114 may be positioned within an image path from the lens 112 such that a visible light image of the surgical field 106 is reflected toward the video camera 122 through the third filter 118. The third filter 118 may be, for example, a 400 nm-700 nm visible light filter. At the same time, the first filter 114 is positioned with the image path from the lens 112 such that a near-infrared image (i.e., the excitation wavelength image) is transmitted toward the near-infrared camera 120 through the second filter 116. The second filter 116 may be an 810 nm +/−20 nm near-infrared emission filter. The filters may be standard or custom-ordered optical components, which are commercially available from optical component suppliers. Other arrangements of filters and other optical components may be used with the system 100 described herein.

The near-infrared camera 120 may be any still or moving image camera suitable for capturing images at the emission wavelength of the excited dye 110. The near-infrared camera may be, for example, an Orca-ER near-infrared camera with settings of gain 7, 2×2 binning, 640×480 pixel field of view, and an exposure time of 20 msec and an effective frame rate of fifteen frames per second. The Orca-ER is commercially available from Hamamatsu Photonic Systems of Bridgewater, N.J. It will be understood that the near-infrared camera 120 of FIG. 1 is only an example. An infrared camera, a far-red camera, or some other camera or video device may be used to capture an diagnostic image, with the camera and any associated filters selected according to the wavelength of a corresponding fluorescent substance used with the imaging system. As used herein, the term "emission wavelength camera" is intended to refer to any such camera that may be used with the systems described herein.

The video camera 122 may be any video camera suitable for capturing images of the surgical field 106 in the visible light spectrum. In one embodiment, the video camera 122 is a color video camera model HV-D27, commercially available from Hitachi of Tarrytown, N.Y. The video camera 122 may capture red-green-blue (RGB) images at thirty frames per second at a resolution of 640×480 pixels. More generally, the near-infrared camera 120 and the video camera 122 may be any device capable of photonic detection and conversion to electronic images, including linear photodiode arrays, charge coupled device arrays, scanning photomultiplier tubes, and so forth.

The display 126 may be a television, high-definition television, computer monitor, or other display configured to receive and render signals from the image processing unit 124. The surgical field 106 may also be a neurosurgical site, with a surgical microscope used to view the surgical field 106. In this embodiment, the display 126 may be a monocular or binocular eyepiece of the surgical microscope, with the near-infrared image superimposed on the visible light image in the eyepiece. In another embodiment, the eyepiece may use direct optical coupling of the surgical field 106 to the eyepiece for conventional microscopic viewing, with the near-infrared image projected onto the eyepiece using, for example, heads-up display technology.

The image processing unit 124 may include any software and/or hardware suitable for receiving images from the cameras 120, 122, processing the images as desired, and transmitting the images to the display 126. In one embodiment, the image processing unit 124 is realized in software on a Macintosh computer equipped with a Digi-16 Snapper frame grabber for the Orca-ER, commercially available from DataCell of North Billerica, Mass., and equipped with a CG-7 frame grabber for the HV-D27, commercially available from Scion of Frederick Md., and using IPLab software, commercially available from Sanalytics of Fairfax, Va. While a Macintosh may be used in one embodiment, any general purpose computer may be programmed to perform the image processing functions described herein, including an Intel processor-based computer, or a computer using hardware from Sun Microsystems, Silicon Graphics, or any other microprocessor manufacturer.

Generally, the image processing unit 124 should be capable of digital filtering, gain adjustment, color balancing, and any other conventional image processing functions. The image from the near-infrared camera 120 is also typically shifted into the visible light range for display at some prominent wavelength, e.g., a color distinct from the visible light colors of the surgical field 106, so that a superimposed image will clearly depict the dye. The image processing unit 124 may also perform image processing to combine the image from the near-infrared camera 120 and the video camera 122. Where the images are displayed side-by-side, this may simply entail rendering the images in suitable locations on a computer screen. Where the images are superimposed, a frame rate adjustment may be required. That is, if the video camera 122 is capturing images at the conventional rate of thirty frames per second and the near-infrared camera 120 is taking still pictures with an effective frame rate of fifteen frames per second, some additional processing may be required to render the superimposed images concurrently. This may entail either reducing the frame rate of the video camera 122 to the frame rate of the near-infrared camera 120 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

Generally, any combination of software or hardware may be used in the image processing unit 124. The functions of the image processing unit 124 may be realized, for example, in one or more microprocessors, microcontrollers, embedded microcontrollers, programmable digital signal processors or other programmable device, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The functions may also, or instead, include one or more application specific integrated circuits, programmable gate arrays, programmable array logic devices, or any other device or devices that may be configured to process electronic signals. Any combination of the above circuits and components, whether packaged discretely, as a chip, as a chipset, or as a die, may be suitably adapted to use with the systems described herein.

It will further be appreciated that each function of the image processing unit 124 may be realized as computer executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. The image processing unit 124 may be deployed using software technologies or development environments including a mix of software languages, such as Java, C++, Oracle databases, SQL, and so forth. It will be further appreciated that the functions of the image processing unit 124 may be realized in hardware, software, or some combination of these.

In one embodiment, the visible light source 102 is a near-infrared depleted visible light source, the excitation light source 104 is a 771 mm, 250 mW laser diode, the dye 110 is indocyanine green or IRDye78-CA, the first filter 114 is a 785 nm dichroic mirror configured to transmit near-infrared light and reflect visible light, the second filter 116 is an 810 nm +/−20 nm near-infrared emission filter, and the third filter 118 is a 400 nm to 700 nm filter. The image processing unit 124 is a computer with software for image capture from the near-infrared camera 120 and the video camera 122, for making suitable color adjustment to the images from the near-infrared camera 120, for making frame rate adjustments to the video camera 122 image, and for combining the two images for superimposed display on the display 126.

The systems described above have numerous surgical applications. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies.

Figure 2:
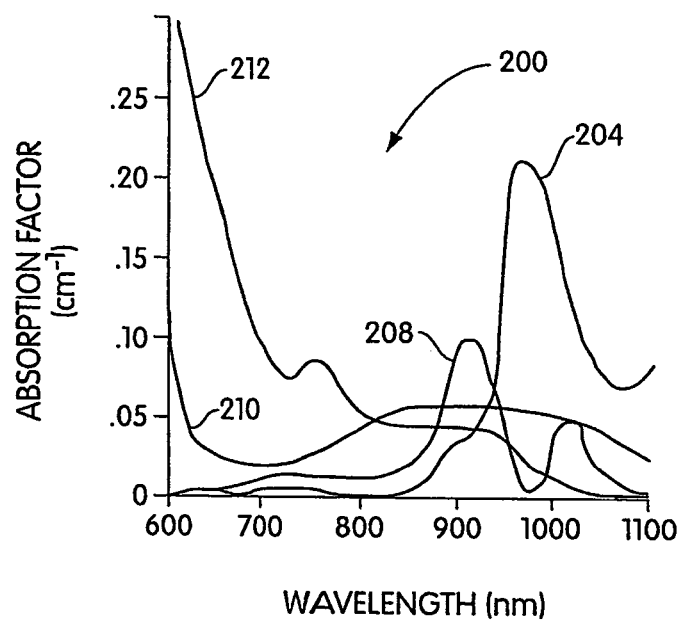
FIG. 2 shows a near-infrared window used by the imaging system.

FIG. 2 shows a near-infrared window used by the imaging system. The near-infrared window 200 is characterized by wavelengths where absorbance is at a minimum. The components of living tissue with significant near-infrared absorbance include water 204, lipid 208, oxygenated hemoglobin 210, and deoxygenated hemoglobin 212. As shown in FIG. 2, oxygenated hemoglobin 210 and deoxygenated hemoglobin have significant absorbance below 700 nm. By contrast, lipids 208 and water 204 have significant absorbance above 900 nm. Between 700 nm and 900 nm, these absorbances reach a cumulative minimum referred to as the near-infrared window 200. While use of excitation and emission wavelengths outside the near-infrared window 200 is possible, as described in some of the examples above, fluorescence imaging within the near-infrared window 200 offers several advantages including low tissue autofluorescence, minimized tissue scatter, and relatively deep penetration depths. While the near-infrared window 200 is one useful wavelength range for imaging, the systems described herein are not limited to either excitation or emission wavelengths in this window, and may employ, for example, far-red light wavelengths below the near-infrared window 200, or infrared light wavelengths above the near-infrared window 200, both of which may be captured using commercially available imaging equipment.

Figure 3:
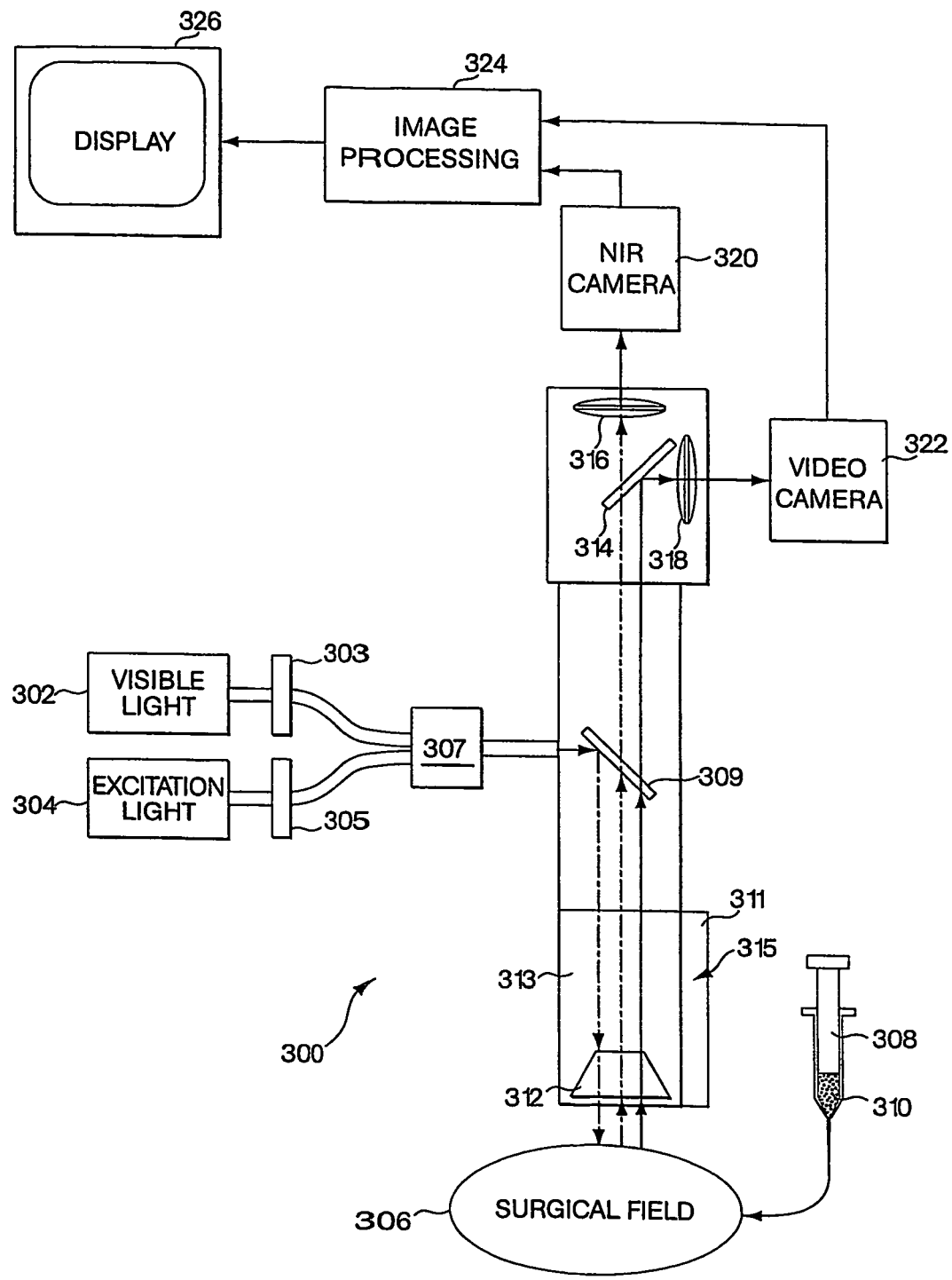
FIG. 3 shows an embodiment of an imaging system for use in an endoscopic tool.

FIG. 3 shows an embodiment of an imaging system for use in an endoscopic tool. The imaging system 300 may include a visible light source 302, and excitation light source 304, a surgical field 306, a dye source 308 containing a dye 310, a lens 312, a first filter 314, a second filter 316, a third filter 318, a near-infrared camera 320, a video camera 322, an image processing unit 324, and a display 326. In general, the visible light source 302 and the excitation light source 304 illuminate the surgical field 306. The dye 310 may be introduced from the dye source 308, such as through injection into the bloodstream of a subject. An image from the surgical field 306 is then captured by two cameras, the video camera 322 capturing a conventional, visible light image of the surgical field 306 and the near-infrared camera 320 capturing a diagnostic image based upon the distribution of the dye 310 in the surgical field 306. These images may be combined by the image processing unit 324 and presented on a display 326 where they may be used, for example, by a surgeon conducting a surgical procedure. In general, each of these components may be any of those components similarly described with reference to FIG. 1 above. Differences for an endoscopic tool are now described.

The imaging system 300 for use as an endoscopic tool may further include a first lens/collimator 303 for the visible light source, a second lens/collimator 305 for the excitation light source 304, an optical coupler 307 that combines the excitation light and the visible light, a dichroic mirror 309, and an endoscope 311 having a first cavity 313 and a second cavity 315.

The first lens/collimator 303, the second lens/collimator 305, and the optical coupler 307 serve to combine the excitation light and the visible light into a single light source. This light source is coupled into the first cavity 313 through the dichroic mirror 309. In one embodiment, the dichroic mirror 309 preferably provides fifty percent reflection of light having wavelengths from 400 nm to 700 nm, in order to optimize an intensity of visible light that reaches the video camera 322 after illuminating the surgical field 306 and passing through the dichroic mirror 309 on its return path to the video camera 322. The dichroic mirror 309 also preferably has greater than ninety percent reflection of wavelength from the excitation light source 304, such as between 700 nm and 785 nm, so that these wavelengths are not transmitted to the cameras 320, 322 after reflecting off the surgical field. Using this arrangement, visible and excitation light sources 302, 304 share the first cavity 313 of the endoscope with the return light path for a visible light image and an emission wavelength image.

The second cavity 315 of the endoscope 311 may be provided for insertion of a tool, such as an optical tool like a laser for irradiation of a site in the surgical field 306, or a physical tool like an instrument for taking a biopsy of tissue within the surgical field. By combining the optical paths of the imaging system 300 within a single cavity of the endoscope 311, the combined gauge of the first cavity 313 for imaging and the second cavity 315 may be advantageously reduced.

The imaging system 300 may instead be used with a laparoscope. Typically, a laparoscope is inserted into a body cavity through an incision, as distinguished from an endoscope which is inserted through an existing body opening such as the throat or rectum. A laparoscope has a different form factor than an endoscope, including different dimensional requirements. Furthermore, use of a laparascope involves at least one additional step of making an incision into a body so that the laparascope may be inserted into a body cavity. The laparoscope may be used with any of the imaging systems described above, and the imaging system 300 of FIG. 3 in particular would provide the benefit of a narrower bore for illumination and imaging optics.

It will further be appreciated that the imaging system 300 may be used to simplify imaging devices other than endoscopes and laparoscopes, such as by providing an integrated, coaxial illumination and image capture device using the techniques described above.

In addition to the surgical applications noted above in reference to FIG. 1, the endoscopic tool of FIG. 3 may be used for direct visualization of malignant or pre-malignant areas within a body cavity, or for image-guided placement of gene therapy and other medicinals to an area of interest within the body cavity.

Figure 4:
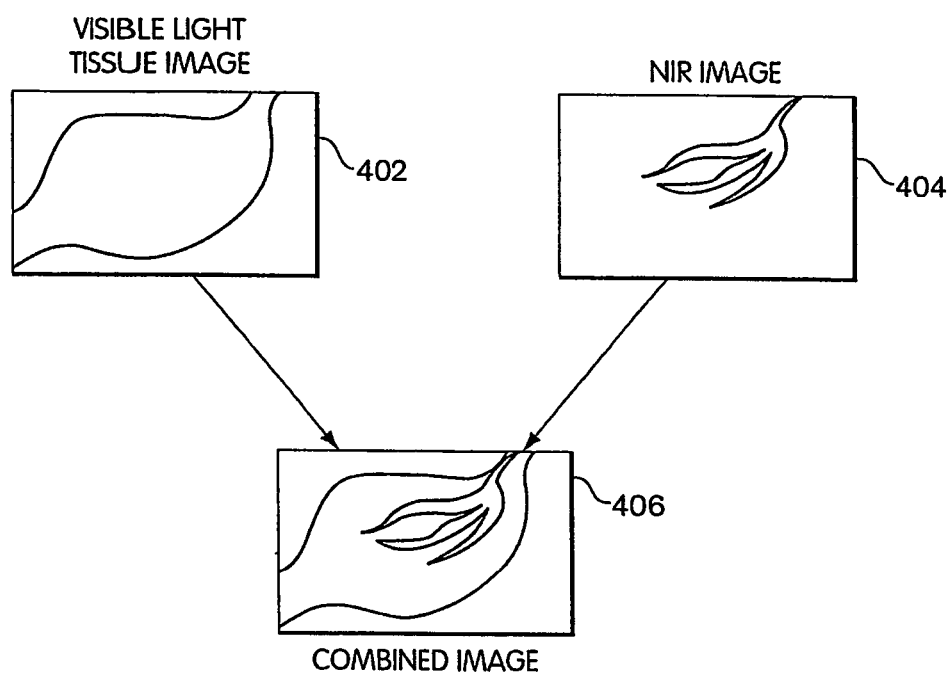
FIG. 4 shows an image displaying both a circulatory system and surrounding tissue.

FIG. 4 shows an image displaying both a circulatory system and surrounding tissue. As described above, a visible light tissue image 402 is captured of tissue within a surgical field. As noted above, the visible light tissue image 402 may include a subset of visible light wavelengths when an optical channel for dye imaging includes a wavelength within the visible light range. A near-infrared image 404 is also captured of the same (or an overlapping) field of view of the surgical field. Although referred to here for convenience as a near-infrared image, it should be clear that the dye-based image 404 may also, or instead, employ other wavelengths, such as far-red or infrared wavelengths. The near-infrared image 404 may be shifted to a visible wavelength for display, preferably using a color that is prominent when superimposed on the visible light tissue image 402. The images 402, 404 may be frame-rate adjusted as appropriate for video display of the surgical field.

The images may be displayed separately as the visible light tissue image 402 and the near-infrared image 404. Or the images 402, 404 may be combined into a combined image 406 by the image processing unit described above. The combined image 406 may then be used as an aid to the procedures described above, or to any other surgical or diagnostic procedure that might benefit from the dye-based imaging techniques described herein.

Figure 5:
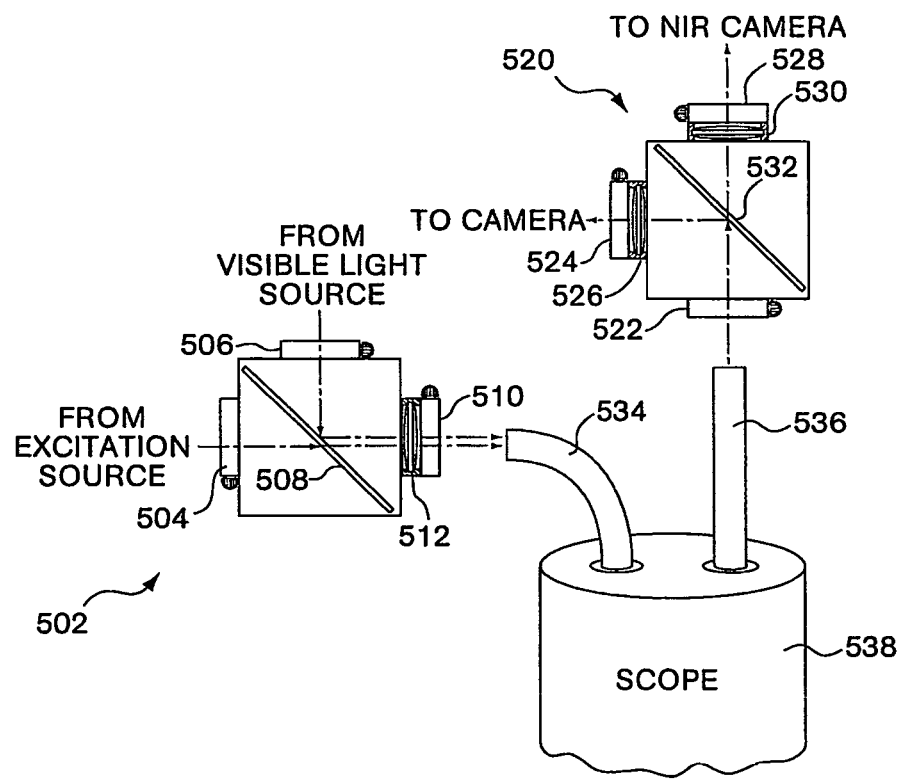
FIG. 5 shows optical hardware that may be used with an imaging system.

FIG. 5 shows optical hardware that may be used with an imaging system. In certain embodiments, such as a conventional endoscope or laparascope, two channels may be provided within the scope for fiber optics that carry a light source and an image respectively. Optical hardware may be used to conveniently connect these light guides to light sources and image capturing hardware used in the systems described above. The hardware may include a light mixer 502 with an excitation light coupler 504, a visible light coupler 506, a dichroic mirror 508, and a mixed light output coupler 510 with a focusing lens 512. The hardware may also include an image separator 520 with an image source coupler 522, a visible light image coupler 524 with a focusing lens 526, a near infrared image coupler 528 with a focusing lens 530, and a dichroic mirror 532. The light mixer 502 and the image separator 520 may be connected to an input 534 and an output 536 of an endoscope 538 or other image source such as a laparascope.

The couplers, more specifically the visible light coupler 506, the excitation light coupler 504, the mixed light output coupler 510, the image source coupler 522, the visible light image coupler 524, and the near infrared image coupler 528 may contain a set screw or other mechanism for securely engaged suitable hardware in a proper position and orientation, and with appropriate light shielding, suitable for use in the imaging system. Additional adaptors may be provided for mating hardware, such as endoscope fibers, to the mixer 502 and separator 520.

The light mixer 502 combines a visible light source, which may be NIR-depleted and/or IR-depleted, or depleted in some other wavelength range for a particular application, with an excitation source, which may be a NIR or IR fluorescence excitation light source or some other light source selected for a particular imaging application. The dichroic mirror 508 may be selected to transmit light from the excitation light source and reflect light from the visible light source, so that a combined light source is passed through the focusing lens 512 into the input 534 of the endoscope 538. While efficient dichroic mirrors may be manufactured that reflect visible light while transmitting light of other wavelengths, it is also possible to construct a dichroic mirror that transmits the visible light instead. Other techniques may combine filters and partial or total reflecting surfaces to similarly combine a depleted white light source with an excitation light source.

The image separator 520 separates the anatomical, or visible light image from a functional image, such as a near-infrared image captured from a dye within the field of view of the scope 538. The images may be separated using, for example, a suitable designed dichroic mirror 532. A focusing lens 526 may be provided for the visible light image, and another focusing lens 530 may be provided for the near-infrared image, so that imaging hardware may be separately connected to each optical port and independently focused.

Thus it will be appreciated that, in one aspect, there is described a method for coupling an endoscope to imaging hardware. More specifically, the output 536 of the endoscope is connected to the image source coupler 522 of the image separator 520, and the other ports 524, 528 of the image separator 520 are connected to suitable imaging hardware. The image provided from the image separator 520 to each piece of imaging hardware may then be independently focused using one of the focusing lenses 526, 530. Once each image has been focused, the images may be aligned by manually rotating the imaging hardware connectors within either or both of the visible light image coupler 524 and the near-infrared image coupler 528. This rotation and focusing may also be accomplished electro-mechanically through the addition of suitable hardware.

It should also be appreciated that the image separator 520 may be used independently, such as in the open systems described above, to provide an adaptable imaging system with readily interchangeable camera connections. The image separator 520 may also be used to connect to a number of different image sources, including an endoscope, a laparascope, a wide angle lens, a zoom lens, or any other optical source or lens. Similarly, the light source 502 may be used to provide readily interchangeable sources of light and replacement of malfunctioning parts. Thus there is provided, through the use of the image separator 520 and/or light source 502, a modular medical imaging system that permits ready interchange and replacement of light sources and imaging hardware.

Such a modular system may be adapted to a wide range of applications. For example, additional optical components may be included, such as a zoom lens on the image source coupler 522. Each of the image separator 520 and the light source 502 may also be constructed to permit convenient access to the interior of the device for cleaning of dichroic mirrors or replacement of the mirrors according to changing imaging requirements. As another example, an X-Y alignment mechanism may be provided in one or more of the couplers from the image separator to permit alignment of the received image from the endoscope and manual registration of received images for each piece of imaging hardware.

Figure 6:
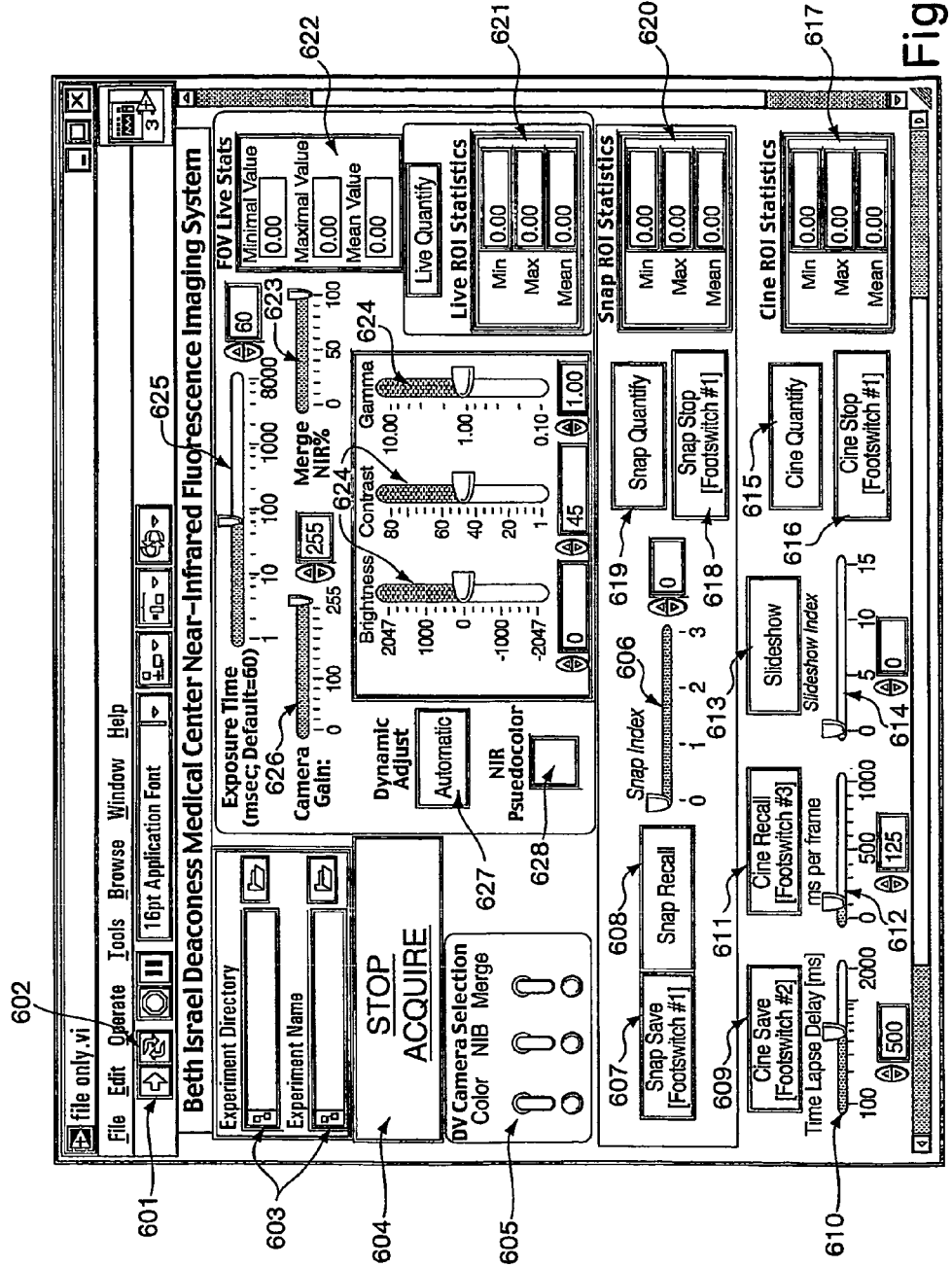
FIG. 6 shows a user interface for an imaging system.

FIG. 6 shows a user interface 600 for an imaging system. It will be appreciated that, while a particular arrangement of user inputs and controls is provided, other arrangements of inputs and controls may be suitably used with the systems described herein to provide the described functionality, and additional features may be provided, or depicted features omitted, according to a particular application. A programming language or combination of programming languages, or a development environment such as LabView, may be used to interface with hardware of the imaging system and provide the functionality described below. The features depicted in FIG. 6 are now described in greater detail.

A start program button 601, which may include a forward arrow or other graphical representation, may be used to begin capturing images from the imaging system. Text fields 603 may be provided to manage image files, including storing to a disk drive and recalling captured images. A browse feature may be provided to navigate an underlying file system of the computer running the interface 600. A naming convention may be employed with files. For example, visible light images may be stored with one suffix (e.g., *.col), while near-infrared or other functional images may be stored with the same file name and a different suffix. A merged visible and functional image may be stored with yet another suffix. Different suffixes or other naming conventions may also be used to distinguish still pictures from moving video.

A stop button 604 may stop an image acquisition, or stop a replay of a stored video. Activating this button may also close all open image windows. Switches 605 may be provided to direct one or more of the possible video feeds (i.e., visible light, diagnostic, or merged video) to a mass storage device such as a separate, and possibly external, CD, DVD, miniDV, tape drive, or other device with storage speed and capacity suitable for storing real-time video. While only one diagnostic image switch is depicted, numerous diagnostic images may be captured simultaneously using different dyes and wavelengths, and a user may select which images to store using the switches 605.

The interface 600 may provide a number of features for capturing and managing snapshots, either still pictures or moving video, during an imaging session. A slider 606 may be provided for selecting among sequential snapshots. A snap save button 607 may be used to store a picture or a segment of video. Footswitches may also be provided and associated with the interface 600 to provide hands-free operation of the imaging system during a procedure such as a surgery. The snap save button 607, may be associated with a first one of such a group of footswitches. A snap recall button 608 may recall a stored snap image. A cine save button 609 may be provided to save a cine image (a continuous, time-lapse movie), and this button 609 may be associated with a second one of the group of footswitches. A slider 610 may be provided in which a user may specify a time interval for capturing cine images, e.g., once every 500 ms. A cine recall button 611 may be used to recall stored cine images. The cine images may also be replayed in a sequential loop using a movie button 613 that toggles between movie and slide show modes of the display. A slideshow index slider 614 may be used to select among a series of sequential cine images. A cine quantify button 615 may be provided to permit quantification of a specific cine image. This button may initiate quantification of an entire image, or present a new window in which specific regions of an image may be selected. The resulting statistics describing, for example, pixel values, may be displayed in a cine statistics box 617 within the interface 600. A cine stop button 616 is provided, and associated with a first one of the foot switches, to stop displaying images in the cine mode. A snap stop button 618 is provided, and associated with a first one of the footswitches, to permit a user to stop snap recording. Stopping the snap in this manner may return the image rendering to live images. A snap quantify button 619 is also provided, similar to the cine quantify button 615, to capture statistics and display them in a snap statistics box 620 within the interface 600. Live statistics may also be provided in a live quantify statistics box 621. Current values, such as pixel values, may be displayed in another box 622.

A number of controls may be provided in the interface 600 to control visual rendering of the images. For example, an opacity slider 623 may be provided to control mixing of a diagnostic and visible light image. The mixing may be specified with a numerical value specifying a percentage opacity for the diagnostic image. Manual image controls 624, such as brightness, contrast, and gamma, may be provided for manual control of the diagnostic image. The manual image controls may be overridden with an automatic button 627. Exposure time for the diagnostic imaging hardware may be manually controlled using an exposure time slider 625. Camera gain may be manually controlled using a camera gain slider 626. A diagnostic image pseudocolor control 628 may be provided to permit a user to select a color in which the diagnostic image, or emission wavelength image, is rendered. The control 628 may be represented within the interface 600 by a square that is filled in with the selected color for pseudocoloring. The control 628 may be linked to a color palette that includes a number of different colors from which a user may select, or a color wheel or other continuous color spectrum from which a user may point and click a desired color. These or other techniques may be used to permit custom selection of the diagnostic image color. Thus a user may vary the diagnostic image color so that it sharply contrasts with naturally occurring colors in the visible light image. Lime green is a useful color for high contrast with living tissue in surgical or other medical imaging applications. Lime green may thus be a default color selection for the pseudocolor of the emission wavelength image, however, any pseudocolor may be used.

Figure 7:
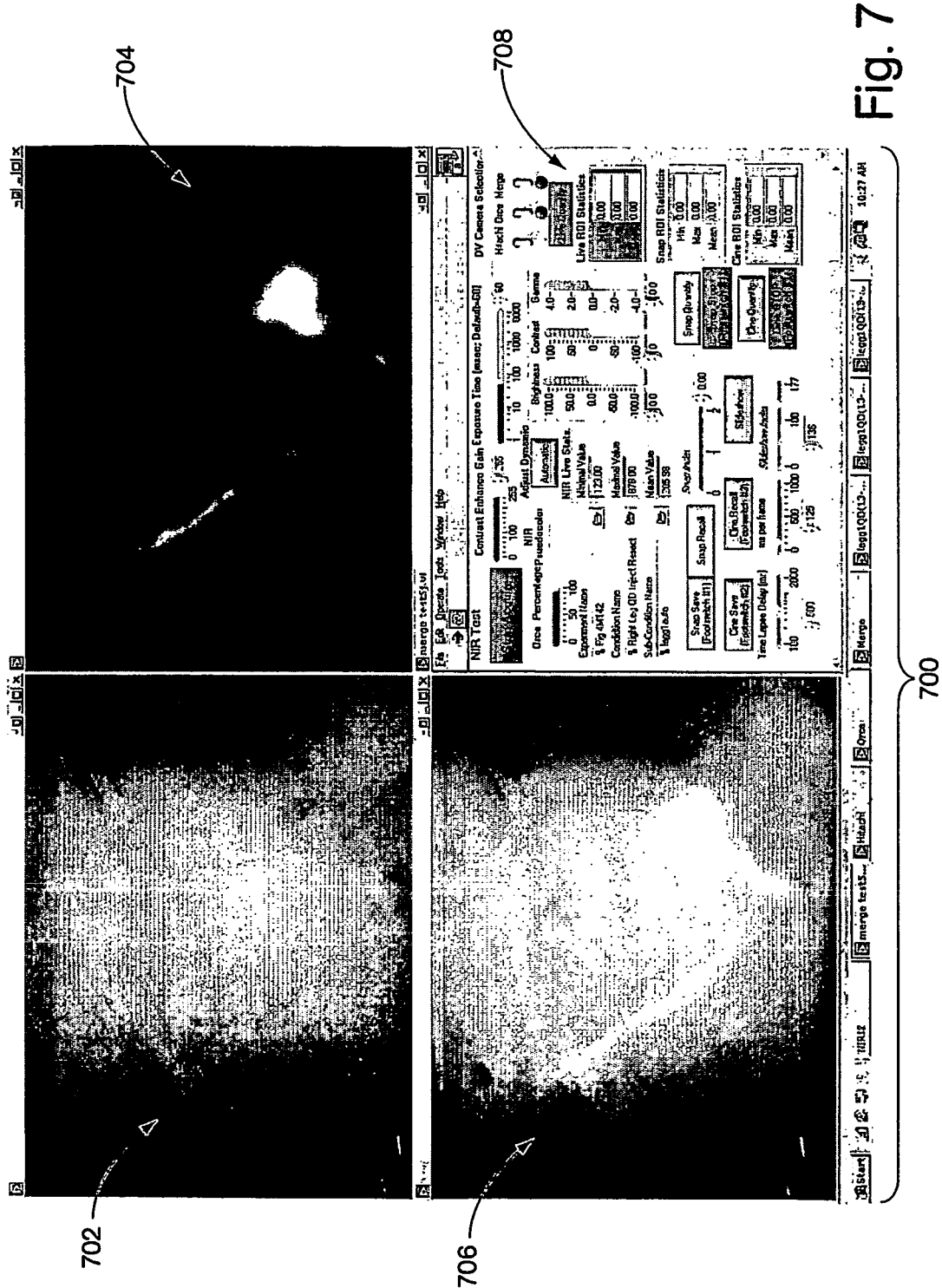
FIG. 7 shows a user interface being used during a surgical procedure.

FIG. 7 shows a user interface 700 being used in a surgical procedure. The interface 700 includes a first window 702 that may display a visible light image captured from a subject (in this case, an anesthetized laboratory animal). A second window 704 may display a functional image captured from an emission wavelength of a substance introduced into the subject (in this case, quantum dots carried by the lymph system). A third window 706 may display a combined image (also referred to herein as a superimposed image or a merged image) of the visible light image and the functional image, as described above, and with pseudocoloring and opacity determined using the interface controls described in reference to FIG. 6. A fourth window 708 may provide a user interface for controlling image capture and display. These four windows may be tiled, as depicted so that each window is fully visible on a display, or some or all of the windows may be cascaded so that one window is fully visible and at least some edge of each other window is visible (and accessible) on some portion of the display. Optionally the windows may displayed over more than one monitor or display, such as by displaying the combined image on one monitor, and the user interface and other images on a second monitor. These and other techniques for displaying multiple windows are well known and may be usefully employed with the interface described herein.

FIG. 7 shows a system employing the above imaging techniques and user interface (and associated functionality) to display a lymph system in a surgical pathology context. In those images, near-infrared quantum dots have been used to map major lymph channels and a sentinel lymph node, permitting excision of the lymph node from surrounding live tissue. One of the significant challenges of surgical pathology is that a target, such as a small tumor or a sentinel lymph node can be very difficult to locate within other tissue, either within a subject or within a specimen surgically taken from the subject. The above system may simplify this process for a pathologist who could use the imaging system to locate the target cells or tissue within a larger section of resected tissue. Thus it will be appreciated that there is disclosed herein a tool for surgical pathology that permits location of pathological tissue within a sample. In such a system, the visible light image may be combined with a pathology image (the image obtained at the emission wavelength) in moving video, and in real time or near-real-time, to provide a surgical tool for locating pathological tissue during ongoing surgery, either within the subject, or within resected tissue from the subject.

Figure 8:
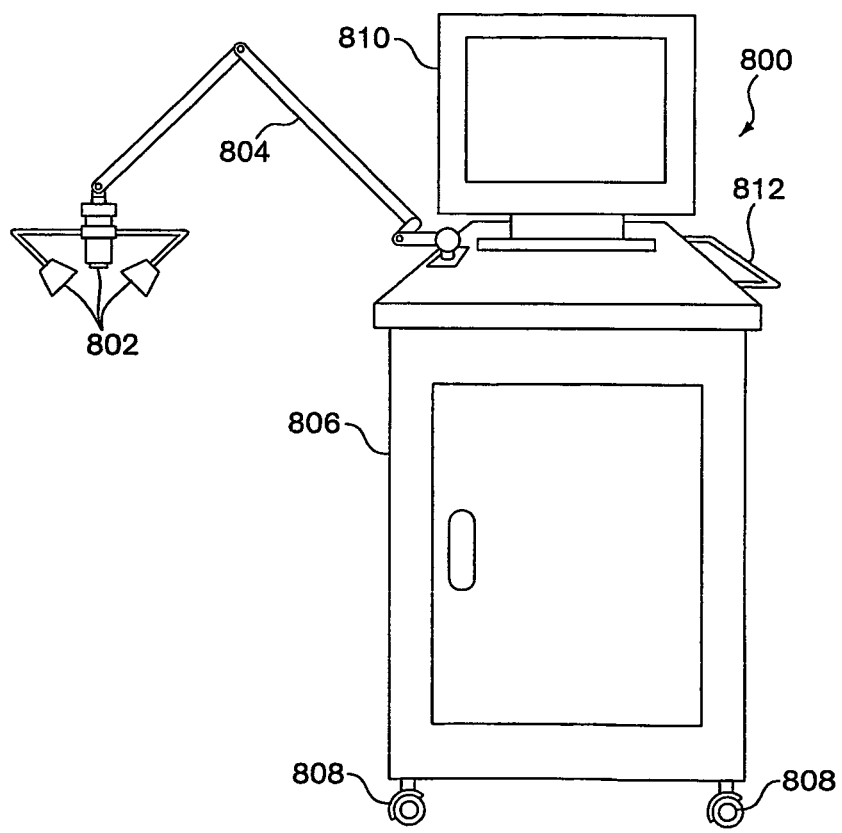
FIG. 8 shows a portable imaging system.

FIG. 8 shows a portable imaging system 800. The elements of the imaging systems described above may be provided as a portable imaging system that contains, within a single cart or other portable structure, all of the cameras, lights, optical links, other hardware, and computer systems to obtain diagnostic images as described above. Cameras and light sources 802 may be attached to an articulated arm 804 providing a range of orientations and degrees of freedom for these optical components. The articulated arm 804 may be counterbalanced with weights or springs to permit low-resistance movement, and may include locking mechanisms at each moving portion so that the cameras and light sources 802 can be secured in a desired location or orientation. Fiber optic links may carry source light and return images to components within a cabinet 806 that houses associated hardware. Where one or more of the cameras is attached to the end of the articulated arm along with the lights, images may be digitally transmitted to the cabinet along suitable cables. Where one or more of the cameras are within the cabinet 806, the images may be optically transmitted to the cameras using fiber optics. A computer, along with a keyboard, mouse, and other input/output devices and data acquisition hardware, may also be included within the cabinet 806, and wheels 808 may be provided for convenient transportation. A display 810 may be provided on top of the cabinet 806 and one or more handles 812 may be mounted to the cabinet 806 for securely handling the portable imaging system 800 in transit. The cabinet 806 may include one or more openings in the back for connecting the system 800 to AC power, and accessories such as the footswitches, additional lenses, optical accessories, tools, and so forth, may be stored within the cabinet 806 while the system is not in use.

It will be appreciated that the above systems and functionality are merely illustrative, and that other dyes, imaging hardware, and optics may be usefully deployed with the imaging systems described herein. For example, an endoscopic tool may employ a still-image imaging system for diagnostic photography within a body cavity. Or any of the imaging systems may be used as described above with excitation and/or emission wavelengths in the far-red spectrum. Through minor adaptations that would be clear to one of ordinary skill in the art, the system could be configured to image two or more functions (i.e., tumor and blood flow) at the same time that a visible light image is captured by associating each function with a different dye having a different emission wavelength. Non-medical applications exist for the imaging system. For example, dyes in a solution form may be sprayed on a mechanical component to identify oxidation, surface defects, or the like. Dyes could also be used to track gas, steam, or air flow through a pressurized system, and in particular to identify leaks around fittings and valves. These and other arrangements and adaptations of the subject matter discussed herein are intended to fall within the scope of the invention.

Thus, while the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the following claims should be interpreted in the broadest sense allowable by law.

What is claimed is:

1. A medical imaging system that captures and displays a visible light image and a diagnostic image of a subject comprising:
    a video camera configured to capture the visual light image;
    at least one near inferred camera configured to capture a diagnostic image; and
    a display configured to display concurrently a video of the visible light image from the video camera, diagnostic image from the at least one near infrared camera, a merged image of the visible light image and the diagnostic image, and a user control interface, the user control interface including:
        a pseudocolor control within the user interface that permits a user to specify a color within a visible light spectrum at which a marker material of a grayscale representation of the diagnostic image of the subject is rendered, wherein said diagnostic image shows a distribution of a marker material within a subject; and
        a frame rates adjustment controlling adjustment of a frame rate of one or more of near infrared cameras and/or the video camera.

2. The system of claim 1 wherein the pseudocolor control includes a color palette of numerous colors from which the user may select a discrete pseudocolor.

3. The system of claim 1 wherein the pseudocolor control includes a display of a continuous spectrum of colors from which the user may select a pseudocolor.

4. The system of claim 1 wherein the user interface further comprises one or more footswitches used to control operation of the medical imaging system.

5. The system of claim 1 wherein the user interface further comprises controls for capturing moving or still images for storage.

6. The system of claim 5 wherein the user interface further comprises controls for replaying stored moving or still images.

7. The system of claim 1 wherein the pseudocolor has a default color of lime green.

8. The system of claim 1 wherein the user interface renders at least two windows selected from a group consisting of a first window showing the visible light image and a second window showing the diagnostic image.

9. The system of claim 8 wherein the diagnostic image is rendered in the second window according to the pseudocolor control.

10. The system of claim 1 wherein a first window, a second window, and the merged image are tiled adjacent to one another within the user interface.

11. The system of claim 10 wherein a fourth window contains one or more controls for the user interface, the fourth window being tiled adjacent to one or more of the three windows.

12. The system of claim 1 wherein the user interface further comprises an opacity control for controlling an opacity at which the diagnostic image is rendered when superimposed on the visible light image in the merged image.

13. A medical imaging system that captures and displays a real time visible light image and a diagnostic image of a subject with an interface rendered on a display, said diagnostic image including a grayscale representation showing a distribution of a marker material within a subject, comprising:
- a video camera configured to capture the visual light image;
- at least one near infrared camera configured to capture the diagnostic image; and
- a display including an interface configured to display concurrently in real time:
  - a first window including one or more controls for the imaging system, wherein the controls include at least a color adjustment that changes a color of a marker material within the diagnostic image to a selected color and a frame rates adjustment for controlling a frame rate of one or more of near infrared cameras and/or the video camera;
  - a second window including the visible light image of the subject from the video camera;
  - a third window including the diagnostic image from the at least one near infrared camera of the subject rendering the marker material in a user selected color; and
  - a fourth window including a merged image superimposing the visible light image and the diagnostic image, the diagnostic image being superimposed using a user-defined color and a user-defined opacity.

14. The system of claim 13 further comprising:
- a visible light source, a fluorescence excitation light source, and an image capture lens attached to a first end of an articulated arm;
- a visible light camera capturing visible light images incident on the image capture lens;
- an emission wavelength camera capturing diagnostic images incident on the image capture lens;
- a computer receiving electronic images from the image capture lens and configured to provide a user interface including a pseudocolor control that permits a user to specify a color within the visible light spectrum at which the diagnostic image is rendered;
- a cabinet housing the computer and attached to a second end of the articulated arm, the cabinet including a plurality of wheels; and
- a display on the cabinet for displaying the user interface.

15. The system of claim 14 wherein at least one of the visible light camera and the emission wavelength camera are within the cabinet.

16. The system of claim 14 wherein at least one of the visible light camera and the emission wavelength camera are at the first end of the articulated arm.

17. The system of claim 14 further comprising a plurality of footswitches used to control operation of the medical imaging system, the plurality of footswitches sized for storage within the cabinet.

18. The system of claim 1, wherein the marker material includes a dye.

19. The system of claim 13 wherein the marker material includes a dye.

* * * * *